United States Patent [19]

DuBose et al.

[11] 4,343,310

[45] Aug. 10, 1982

[54] APPARATUS FOR REMOVING APPENDAGES FROM AVIAN SPECIES

[75] Inventors: Ronald A. DuBose, Marietta, Ga.; William D. Woolsey, Greenville, Tenn.

[73] Assignee: Agri-Bio Corporation, Ithaca, N.Y.

[21] Appl. No.: 162,554

[22] Filed: Jun. 24, 1980

Related U.S. Application Data

[62] Division of Ser. No. 906,808, May 17, 1978, Pat. No. 4,237,891.

[51] Int. Cl.³ .............................................. A61B 17/36
[52] U.S. Cl. ................................................. 128/303.14
[58] Field of Search ........... 128/303.1, 303.14, 303.17, 128/792; 219/221, 233; 30/140; 83/170, 171

[56] References Cited

U.S. PATENT DOCUMENTS

| | | | |
|---|---|---|---|
| 3,302,645 | 2/1967 | Lockmiller | 128/303.1 |
| 3,390,679 | 7/1968 | Turner | 128/303.1 |
| 3,570,487 | 3/1971 | Reynolds | 128/303.1 |
| 3,812,857 | 5/1974 | Lyon | 128/303.1 |
| 4,040,425 | 8/1977 | Goodling et al. | 128/303.14 |

*Primary Examiner*—Lee S. Cohen

[57] ABSTRACT

A method and apparatus for removing appendage tissue from avian species such as domestic fowl and principally from commercial chickens and turkeys is disclosed. When the appendage is the beak, the method is known as debeaking and the invention is a method comprised of the step of burning and simultaneously cauterizing a hole through a portion of a bird's beak in order to damage the tissue and precipitate eventual rejection thereof outwardly from the point of damage, and apparatus which includes a face mask for positioning the bird's beak between and in contact with opposing electrodes projecting into the apparatus which effect the burning as aforesaid. A power source for the electrodes provides an open circuit voltage of sufficient magnitude to initiate current flow through the beak when opposing sides of the beak contact the electrodes. With current flow initiated, the power source current increases toward a maximum short circuit value sufficient to cause burning of the portion of the beak between the electrodes, while the voltage drops to a value sufficient to maintain the desired current. The preferred control for the power source determines a time integral of current flowing through the bird's beak and, upon reaching a predetermined time integral of current value, the control de-energizes the power source.

2 Claims, 10 Drawing Figures

Fig. 9

APPARATUS FOR REMOVING APPENDAGES FROM AVIAN SPECIES

This is a continuation, division, of application Ser. No. 906,808, filed May 17, 1978, now issued as U.S. Pat. No. 4,237,891.

BACKGROUND OF THE INVENTION

1. Field of the Invention

This invention relates to a method and apparatus for removing appendages from avian species. More specifically, this invention relates to removing a portion of the beak of a domestic fowl, in particular, commercial chickens and turkeys.

In the poultry industry, losses primarily occur in flocks from disease and cannibalism. In the latter regard, birds confined in common close quarters exhibit a tendency to peck each other around the comb and/or tail regions and pull feathers. When the pecking produces a break in a bird's skin and a blood spot appears, other birds will constantly peck the bird until it is killed. Although this phenomena is not as telling as the occurrence of a disease might be, the loss of a few birds on a daily basis increases to significant numbers in the poultry meat and egg producing industry.

2. Discussion of Prior Art

In an effort to eliminate cannibalism and thereby reduce bird losses, various debeaking apparatus have been designed for the poultry industry. Such devices have generally employed either a knife device to amputate a portion of the bird's beak or a heated knife to blunt and damage or remove the tip of the beak.

Among the various devices which have been made available to the industry, those referred to hereinafter are representative of those in the prior art and generally describe those which have been devised in an attempt to provide poultrymen with a satisfactory apparatus.

U.S. Pat. No. 3,390,679 issued to Leon C. Turner discloses a beak trimming device whereby the upper and lower beaks are trimmed simultaneously. When employing this device, care must be exercised by the use of a tongue depressor to avoid amputating the bird's tongue.

U.S. Pat. No. 3,302,645 issued to Jesse W. Lockmiller is concerned with a combination debeaking-vaccinating device for performing the two operations at the same time.

U.S. Pat. No. 3,812,857 issued to James Lyon utilizes a heating cutting and cauterizing blade which shears off and cauterizes the end of the beak.

U.S. Pat. No. 3,570,487 issued to Lamar W. Reynolds also employs a combination cauterizing element and vaccinator with an attached counting device. As in other devices of this type, the operator must place his thumb at the base of the skull and his forefinger around the base of the lower beak and gently squeeze to force open the beak of the bird.

U.S. Pat. No. 4,040,425 issued to John S. Goodling and Gayner R. McDaniel discloses a poultry beak remover whereby an electric potential generates a spark across the top of a bird's beak to burn a portion thereof.

While the devices disclosed above have sought to solve the problem of effectively and efficiently debeaking poultry, the results have not been satisfactory. The efficiency of the devices is related in part to the skill of the operator. Accordingly, there is a wide variation in debeaking uniformity, effectiveness and permanency. Moreover, the devices often impart a significant trauma and initial beak tenderness which impairs normal feeding and weight gain in young birds.

The foregoing limitations are exacerbated in reference to the broiler industry where the economics of handling birds which will be marketed in eight weeks or so dictates debeaking the bird at the hatchery even though the bird is only a day or two old. At this age the bird is small and somewhat fragile. Accordingly, the debeaking process tends to be somewhat guarded and frequently ineffective.

In raising pullets the above situation is partially relieved by allowing the chick to reach an age of six days or more before debeaking. The difficulty with this partial solution, however, is that the chicks must be manually caught which is time-consuming and expensive.

The foregoing brief description of the problem in the art to which the present invention is addressed, particularly those for providing means for effectively and efficiently debeaking birds, is overcome by the provision of the novel debeaking apparatus and method of the present invention described hereinafter in detail. The term "debeaking" as used herein refers to the removal of a portion of the upper or lower beak or to the removal of a portion of both beaks sufficient to reduce or eliminate the use of the beak in pecking other chicks and other reasons described herein, and not necessarily to removal of the entire beak as the term might literally denote.

Also, it should be understood that while the following description is concerned with removing a portion of the upper beak from young fowl, the removal of a portion of the lower beak is also within the purview of the present invention. The simultaneous debeaking of a portion of the upper and lower beaks is also within the purview of and is readily effected by the present invention. The present invention also contemplates the removal of a toe or toes from a male to prevent injury to a female during mating, from a female to prevent injury when housed in a cage, as well as removal of a toe or toes from both male and female for identification purposes. The term appendage is therefore used herein to generically define the class of members or parts thereof which may be removed from fowl. In view of the overwhelming commercial application to debeaking, the latter is only described herein in detail.

OBJECTS OF THE INVENTION

Objects of the invention are to provide:

Novel apparatus for removing appendages from avian species.

Novel apparatus for debeaking poultry wherein the debeaking operation may be accurately performed at a rate greater than previously known systems.

Novel apparatus which will enhance the uniformity of the debeaking process even in connection with birds having beaks with slightly variant physical dimensions.

Novel apparatus which will minimize trauma to the bird and disruption to the bird's ability to eat and drink immediately following the debeaking operation.

Novel debeaking apparatus which is sanitary and reduces the degree of odor emitted by at least some previously known devices.

Novel apparaus for debeaking fowl which is safe to operate.

Novel debeaking apparatus which may advantageously be accurately utilized by operators with a minimum amount of training and prior experience.

A novel system for removing undesired portions of appendages from avian species, particularly for debeaking fowl, comprising mask apparatus for receiving and positioning the beak of the fowl, the mask apparatus having a recess element through which a portion of the beak extends with the beak received by the mask apparatus, and apparatus in communication with the portion of the beak extending through the recess element for applying energy through the interior of the portion and selectively damaging a portion of the interior extending from one surface to an opposing surface of the beak by heating in the interior, the energy applied being of sufficient magnitude to damage the interior portion by burning without effecting the immediate removal of the undesired portion.

Novel debeaking apparatus which may be facilely adjusted to accommodate electrode usage and wear.

Novel debeaking apparatus which exhibits a long operational life without requiring frequent replacement of key operating elements.

BRIEF SUMMARY OF A PREFERRED EMBODIMENT

A preferred embodiment of the subject invention which is intended to accomplish at least some of the foregoing objects comprises a debeaker having a mask and mask holder connected to a control and power housing. A pair of electrodes extend from the housing through the mask holder and project into the mask for direct contact with opposing lateral surfaces of a bird's beak, preferably the upper beak. The electrodes are energized by a power source having characteristics such that there is initially supplied an open circuit voltage of sufficient potential to cause the initiation of current flow through the bird's beak upon contact of the electrodes by the opposing surfaces of the beak. Upon initiation of current flow, current flow rapidly increases to a value sufficient to cause burning of the portion of the beak between the electrodes. The power supply is such that the current value will be sufficient to cause burning but will not exceed a predetermined maximum short circuit value. As current flow increases, the voltage across the electrodes drops toward a value sufficient to maintain current flow at the sufficient burning value but substantially lower than the open circuit voltage value.

It will be appreciated by those skilled in the art that control of the power supply between on (energized) and off (de-energized) conditions may be accomplished in various ways. In the preferred control of the invention, time integral of current is directed from the electrodes through the bird's beak to damage the beak by resistance heating. The time integral of current is monitored by the control unit and upon reaching a predetermined level the electrode circuit is opened by a suitable electronic switch to terminate the debeaking process. Within a few days the bird's beak will further deteriorate at the resistance point and the tip of the upper beak will fall off, leaving a blunted upper beak.

It will be appreciated that the apparatus and method according to the invention provides a substantially uniform and controlled amount of energy to the beak of a bird, thereby enhancing uniformity and quality of the debeaking process. The energy applied to the bird's beak burns a hole through the beak in such a manner that the young bird suffers minimal trauma and simultaneously cauterizes the tissue. Debeaking by use of the invention moreover does not prevent the bird from partaking of solid and liquid nourishment during the initial growth period. The novel apparatus and method further provides for a maximum debeaking process and effectively protects the operator from the high voltage used in the process.

Moreover, it will be seen that various portions of appendages, e.g., a portion of both the upper and lower beaks may be removed by placement of the beak so that the electrodes contact the top of the upper beak and the bottom of the lower beak at the same time. Also, various appendages may be removed by appropriate modification of the mask to properly receive and guide the particular appendage being removed. The mask can also be molded to conform to the shape of the appendage which is to be removed.

THE DRAWINGS

Other objects and advantages of the present invention will become apparent from the following detailed description of a preferred embodiment thereof taken in conjunction with the accompanying drawings, wherein:

FIG. 7 is a schematic representation of a power circuit and control system in accordance with a preferred embodiment of the invention:

DETAILED DESCRIPTION

Figure 1:
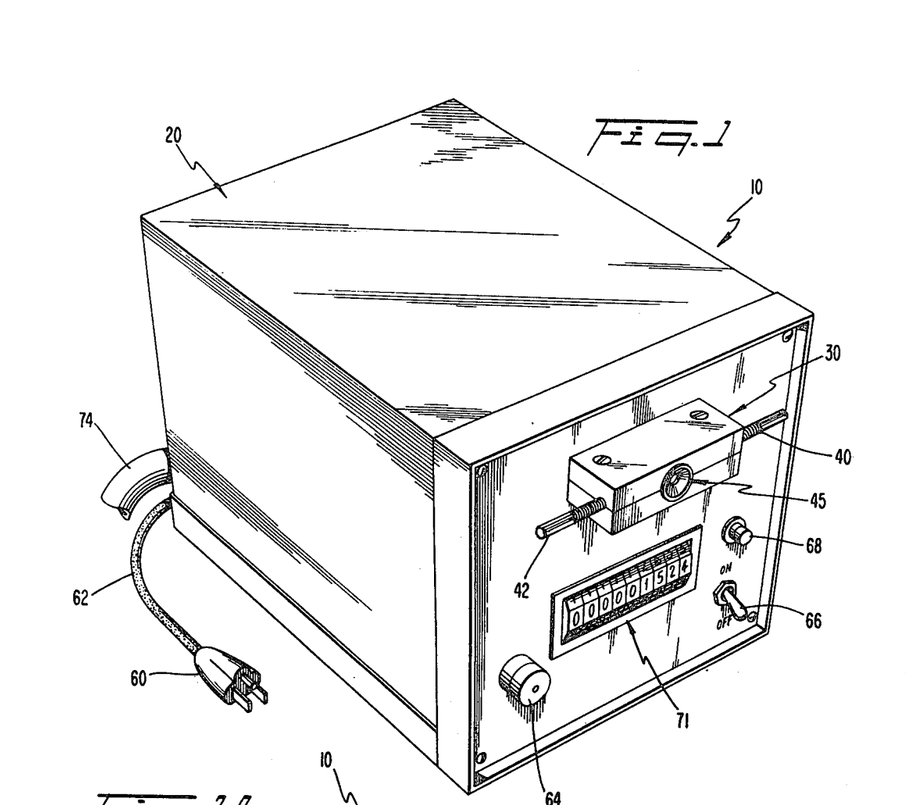
FIG. 1 is a perspective view of one embodiment of the invention including a housing for containing electrical power apparatus and controls, and a burn unit attached thereto for receiving the beak of a young chick.

Referring now to the drawings, and particularly to FIG. 1, the preferred appendage removal apparatus, debeaking apparatus 10, is shown comprised generally of a power and control unit 20 and a novel burn module 30 having electrodes 40 and 42 located on opposite sides thereof, and a chick receiving mask means generally indicated as 45 on the front wall thereof. The power and control unit 20 is adapted to utilize a conventional source of electric current (e.g., 110 volt, 50 or 60 cycles) to power the debeaker. Accordingly, a grounded plug 60 and flexible conductor 62 are input to unit 20 through fuse 64 and power on-off switch 66.

On the front panel of the power and control unit housing is fitted an indicator lamp 68 suitable to signal when the apparatus is "on" and in a ready conditin.

Also, a suitable conventional counter 71 may be provided to keep track of the number of birds debeaked.

Figure 2A:
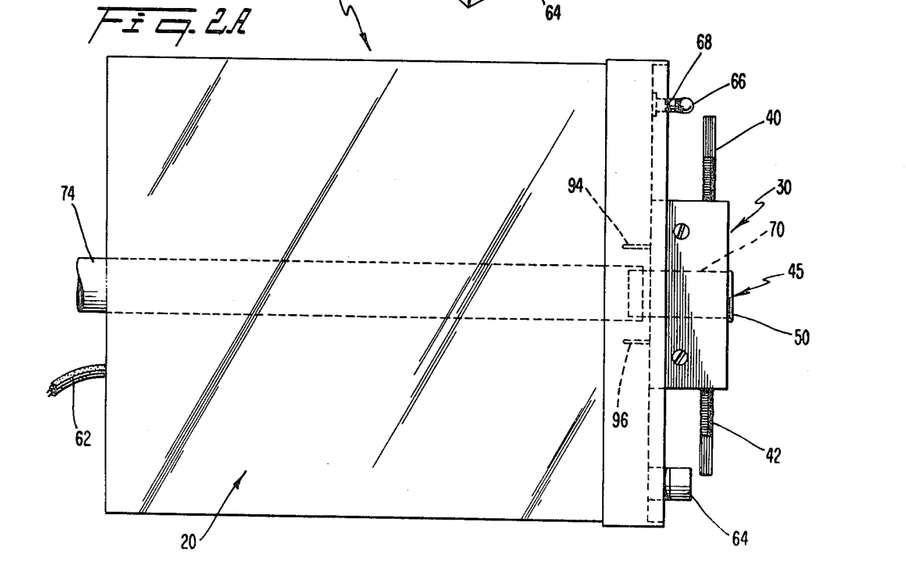
FIG. 2A is a plan view of the debeaking apparatus of FIG. 1.

Referring to FIG. 2A, the mask means 45 is comprised of a frontal face mask 50, preferably formed integrally with an exhaust tube 70 which feeds into an exhaust conduit 74.

The exhaust conduit 74 may be connected to any conventional source of negative pressure, not shown. Accordingly, ambient air may be drawn into the exhaust system through the mask to cool the electrode tips and remove any vaporized beak matter through tube 70.

As will be described hereinafter in greater detail, the electrodes 40 and 42 extend adjustably into the exhaust tube 70 immediately behind the face mask 50. These electrodes are connected to the power source (FIG. 2B) through the provision of connector pins 94 and 96 that engage the electordes and provide an electrical path thereto.

Figure 2B:
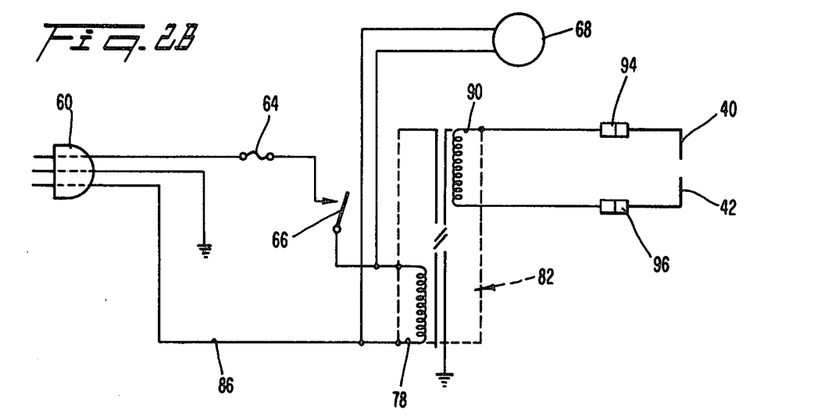
FIG. 2B is a schematic circuit diagram of a preferred power source and electrode arrangement according to the invention.

The debeaker and a preferred form of a power supply system is shown schematically in FIG. 2B. The grounded plug 60 is operable to connect to an alternating voltage source through the fuse 64 and the on-off switch 66 to a primary winding 78 of a grounded super isolation constant current step-up transformer 82 having very low primary to secondary capacitance. The secondary winding 90 of the isolation transformer 82 is connected through the connector pins 94 and 96 to the electrodes 40 and 42 as was mentioned previously.

It can be seen that the transformer 82, when energized, is the power source for the electrodes 40 and 42. The application of power to the transformer and thus to the electrodes is, of course, controlled by the switch 66 but may alternatively be controlled by an automatic control ciucuit as is hereinafter described. One aspect of the invention involves the power source and electrode arrangement and it will be appreciated that various controls may be used in conjunction therewith. For example, control may be accomplished by a conventional analog or other type timing circuit that detects the initiation of current flow to the electrodes and de-energizes the power source or otherwise cuts off current flow after a predetermined time period.

To provide the desired voltage/current characteristics, the power source preferably has an interdependent voltage/current characteristic such that a first voltage of sufficiently high value to initiate current flow through the fowl's beak with the beak in contact with the electrodes (e.g., 1200 volts) is initially present between the electrodes 40 and 42 with no current flowing between the electrodes. This voltage may be referred to as the open circuit output voltage of the power source.

When the beak is inserted between the electrodes, current flow is initiated between the electrodes through the beak. The power source characteristics are such that this current flow is limited to a predetermined maximum root mean squared value (e.g., 1.5 amperes). This maximum current value, which may be reached if the beak provides a low resistance of several hundred ohms or less between the electrodes, may be referred to as the short circuit output current.

According to a preferred embodiment of the invention, a power source having the foregoing characteristics is provided by employing a constant current 10:1 step-up super isolation transformer which is designed to operate from a 120 volt input and provide a 1200 volt no-load or open circuit output voltage. The short circuit characteristics of the transformer are such that it supplies about 1.5 amps to a range of loads between zero and several hundred ohms. Thus, a high voltage, current initiating potential is provided at the electrodes, and the virtual short circuit formed across the electrodes through the beak causes a maximum of about 1.5 amperes to flow through the beak.

It can be seen that the super isolation constant current transformer 82 eliminates the likelihood that an operator could receive a detectable shock from the subject invention and thus significantly enhances safety and operator acceptance of the device. Moreover, highly desirable burning results are achieved in a readily controllable manner.

Figure 3:
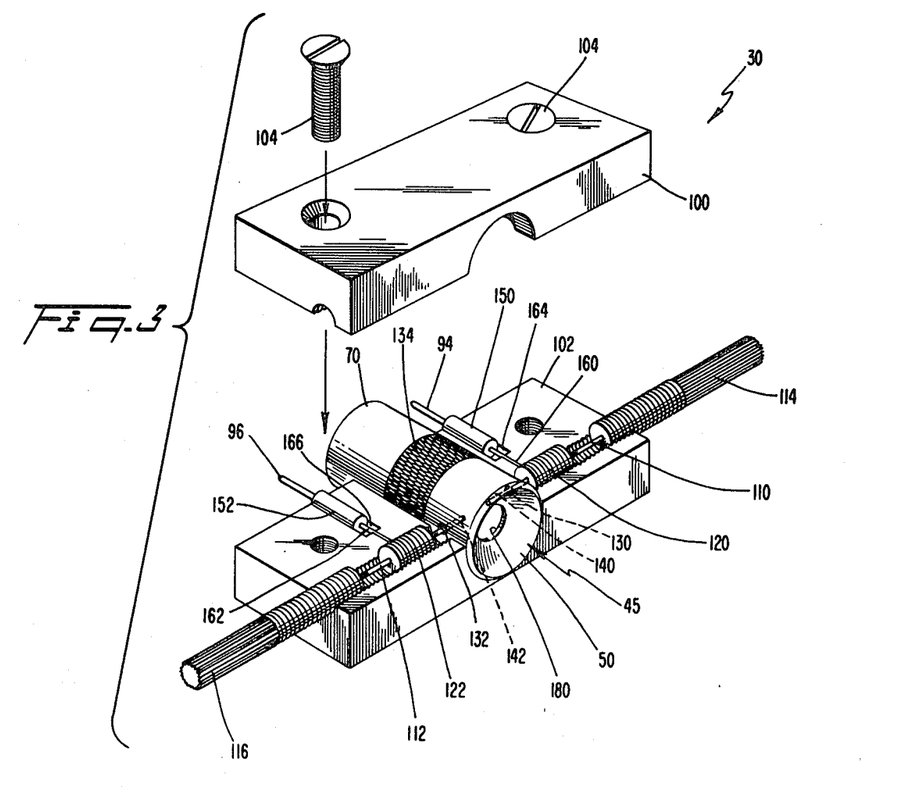
FIG. 3 is a perspective vew of the debeaker burn module partially disassembled.

Referring now to FIG. 3, the burn module is shown in detail in accordance with the preferred embodiment of the invention.

Burn module 30 is comprised of upper and lower blocks 100 and 102, preferably of relatively hard, heat resistant, nonconductive plastic, ceramic, or similar material. The blocks are designed to sandwich together, being held by conventional threaded fasteners 104. Also, as shown, the blocks are suitably molded or bored to receive mask means 45 and hold in place the various components of the burn module when assembled together as shown in FIG. 1.

Figure 4:
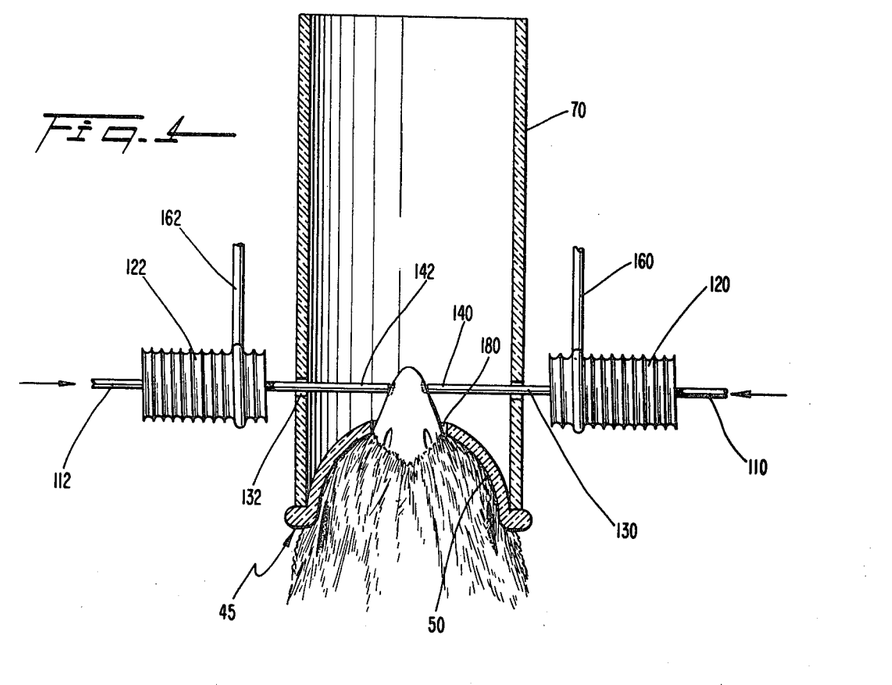
FIG. 4 is a sectional plan view taken along the horizontal mid-point of the mask means including a pair of opposing adjustable electrodes and diagrammatically showing a chick with beak between and in contact with opposing electrodes ready for treatment.
Figure 5:
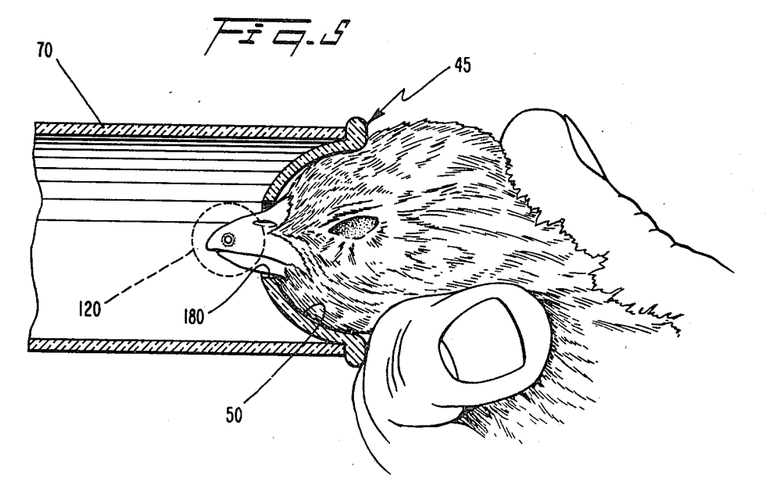
FIG. 5 is a side plan view of the mask showing the position of a bird's beak and the desired effect of the burn operation.

The electrodes 40 and 42 are comprised of metallic rods 110, 112, preferably of tungsten or other long-lasting material, adjustably held on opposite sides of tube 70 by non-conductive thumb screws 114, 116 threaded into blocks 100, 102, and by fixed metallic conductor bushings 120, 122. These metallic rods extend through bushings 120, 122 to project into the mask means through apertures 130, 132 in tube 70 immediately behind mask 50. Apertures 130, 132 are shown as round holes of slightly larger diameter than rods 110, 112. Tube 70 can contain several apertures 130, 132 spaced longitudinally or apertures 130, 132 can be a single elongated aperture. Metallic rod terminals 140, 142 are therefore established in substantially opposed spaced-apart relationship within tube 70 as is best illustrated in FIGS. 4 and 5. The position of the terminals with respect to apertures 130, 132 can be varied as desired depending on bird size and species by adjusting mask means 45 inwardly or outwardly with respect to blocks 100, 102. A knurled section 134 on tube 70 may be provided to increase the friction hold of the mask means in the burn module.

The connector pins 94 and 96 extend through mounting collars 150 and 152 to leads 160 and 162 which, in turn, project through the hollow routed zones 164 and 166 and into electrical contact with metallic cylindrical bushings 120, 122, thus supplying electrical communication with the power source as described above in connection with FIG. 2B. The tips of leads 160 and 162 are connected to the bushings. The cylindrical bushings 120, 122 intimately fit and are held by blocks 100, 102, within a suitable bore as shown and are provided with axial central bores dimensioned to receive in intimate electrical contact electrode rods 110, 112 which, as mentioned above, are operably translated toward and away from each other by manipulation of the thumb screws 114, 116. The optimum spaced apart relationship of the terminals will vary depending upon the bird species being processed and the location of the burn desired. Since it is desired, in the preferred embodiment of the invention, to burn a substantially cylindrical hole in the upper beak, an electrode rod 110, 112 of round cross section is used; however, electrodes of other cross sectional configurations may be employed. Debeaking mask 50 is generally shaped and adapted to receive the chick face whereby the beak can protrude through an opening 180 and into contact with electrode terminals 140, 142. Mask 50 and tube 70 are preferably made from quartz, although hard glass or another material such as alumina or lava having the properties of being heat-resistant and long-wearing for repeated usage up to several thousand times per day are also suitable.

In operation an operator axially adjusts the mask means 45 and positions the electrode tips such that proper location of terminals 140, 142, which may be bent or otherwise physically adjusted if need be, is achieved for the size of the birds to be debeaked. Thus, the terminal tips are spaced apart the approximate thickness of the beak anticipated and at a level adjacent the portion of the beak to be removed. The unit is energized by actuation of switch 66 which turns on lamp 68 to signal a ready condition.

A chick's beak is then funneled into mask 50 and into direct physical contact with the terminals 140, 142 of the electrodes (as shown in FIGS. 4 and 5).

This completes the circuit and current is passed through the bird's beak which burns a hole through the beak by resistance heating. The burning operation will typically entail less than one second to sufficiently damage the beak tissue and concomitantly cauterize the interior surface. Within a few days the tip of the upper beak will slough off.

It can be seen that with the embodiment of the invention illustrated in FIGS. 1 and 2B, the power source is energized as long as the switch 66 is closed. Thus, the operator must control the duration of current flow through the bird's beak either by removal of the beak from the mask 50 after a brief period or by opening the switch 66 after such period (removal of the beak being preferred). This type of operation is quite satisfactory for most applications of the invention, particularly since the relative simplicity of the system makes it quite economical both in initial cost and to operate. Of course, a certain amount of operator skill is required and slightly differing total electrical energy levels may be applied to the beaks of the birds due to differences in time of application, total current value reached, etc.

Accordingly, automatic control of the power source may be provided either on a fixed time basis as was previously indicated or on the basis of a time integral of current as is described hereinafter in connection with FIGS. 6-9 wherein like numerical designations have been used to signify elements previously discussed.

Figure 6:
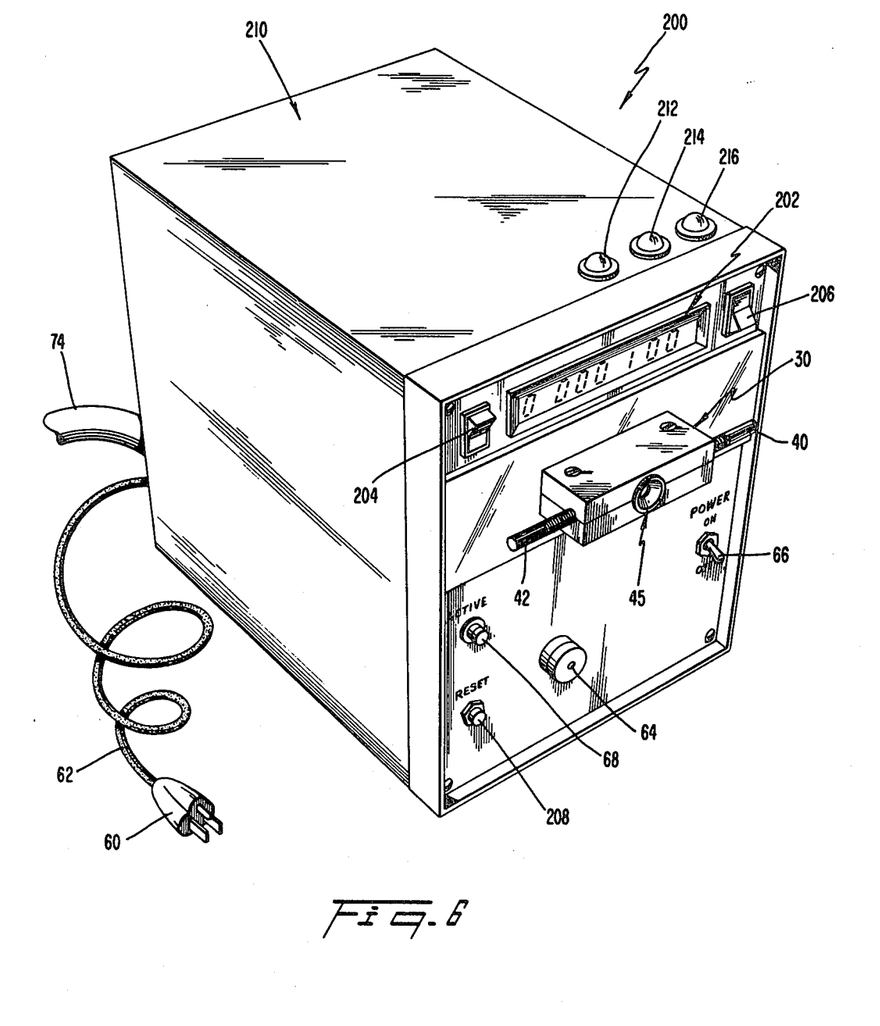
FIG. 6 is a perspective view of another embodiment of the invention including a housing and a burn unit, wherein control of the unit is automatic.

Referring now to FIG. 6, the debeaking apparatus 200 generally comprises a power and control unit similar to that shown in FIG. 1 except that additional controls and indicators have been added. The unit includes the burn module 30, electrodes 40 and 42 located on opposite sides thereof, and the chick receiving mask means 45 previously described. The power and control unit is adapted to utilize a conventional source of electric current to power the subject debeaker. Accordingly, the grounded plug 60 and flexible conductor 62 are input to the unit through the fuse 64 and a power on-off switch 66 as in the FIG. 1 embodiment.

The control unit is fitted with an indicator light 68 suitable to signal when the apparatus is on and with an array of photo-decimal display windows 202 to provide a decimal or other suitable display of desired information with a plurality of light emitting diodes or the like. This visual display array may be programmed to present a variety of parameters such as the total number of debeaks performed since the unit was turned on; the number of debeaks in a batch, i.e., 100 chicks per box is typical; the energy content of the burn; the rate of debeaks per hour based on the previous two minutes, etc.

Display control is effected through a rocker switch 204 which may be rolled up or down to select the display. Once selected the display may be modified by rolling a second rocker switch 206 up or down. Further, a batch count reset switch 208 may be utilized to zero a batch count as desired.

The top panel 210 is also fitted with a burn complete light 212, an optional batch count alarm 214 and a ready light 216, which indicates when an operator should insert a bird's beak into the mask means 45.

Referring now to FIG. 7, there will be seen a schematic representation of a preferred form of a debeaker control system in accordance with the invention.

The grounded plug 60 is operable to connect to a conventional domestic power source to the transformer 82 which supplies the electrodes 40 and 42 as described previously. The circuit for current flow through the primary winding may be interrupted by a suitable conventional solid state relay 222 which is controlled by a control circuit 246. Power for the logic and other circuits in the circuit 246 is supplied through a transformer 240 that feeds a regulator 242 in a conventional manner. The power regulator 242 in turn provides power to drive a microcomputer 244 mounted upon a printed circuit board 247.

In addition to the safety provided by the isolation transformer 82 previously described, appropriate interlocks may be provided for the protection of the operator. For example, an interlock 236 may be connected to the case, requiring that the case be closed and secure before the debeaking operation may begin.

Current blowing through the electrodes 40 and 42 is continuously monitored by a current transformer 248 which feeds into an analog to digital converter 250.

Figure 8:
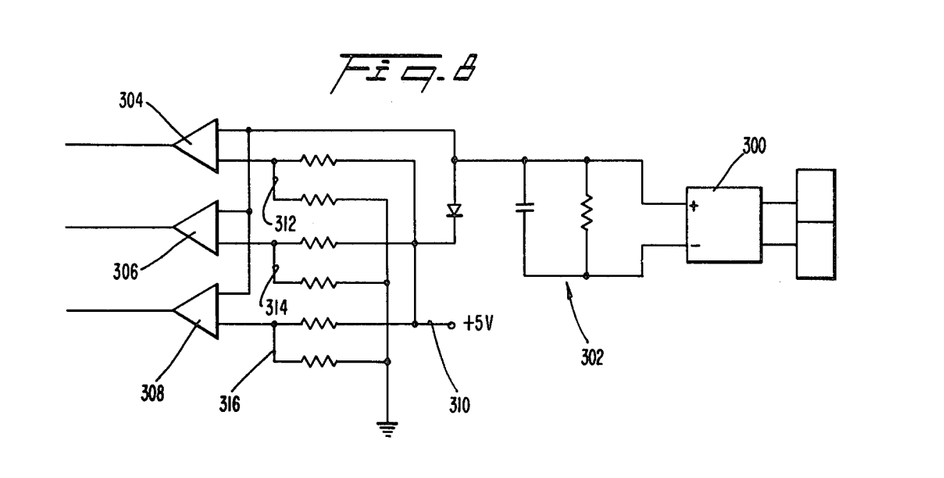
FIG. 8 is a schematic of an analog to digital converter circuit for monitoring current flow through a bird's beak.

In this connection, FIG. 8 is a schematic representation of an analog to digital converter in accordance with a preferred embodiment of the invention. More specifically, AC output current from the secondary of the current transformer 248 is fed into a bridge rectifier 300. Output from the rectifier is fed through an RC filter 302 creating a pulsating DC voltage proportional to the current flowing in the beak which is fed into the high side of a series of comparators 304, 306 and 308.

A five volt reference voltage is received from the power regulator as at 310 and is input into a series of resistive divider circuits 312, 314 and 316 which in turn provide a reference voltage into the low side of the comparators 304, 306 and 308. The resistances in the resistive divider circuits 312, 314 and 316 are sized to input a value into the low side of comparator 304 which is 40% of full power current in the input line. In a similar manner the low side of comparators 306 and 308 are provided with 60% and 80% respectively of full power current in the input line.

A comparison is made between the monitor current in the input line with the 40%, 60% and 80% threshold values each half cycle of the input current. If a current greater than 40% of the optimum current value is monitored through the input line, then a binary signal of 0011 having a decimal value of 3 will be transmitted to the microcomputer 244. If the measured current value is greater than 60% of optimum, then a binary signal of 0111 (having a decimal value of 7) will be transmitted to the microcomputer. Finally, if the measured current value is greater than 80%, then a binary signal of 1111

(having a decimal value of 15) is input to the microcomputer each half cycle.

The microcomputer 244 is of a known commerical design and includes a conventional microprocessor unit, powered by 12 and 5 volts, d.c., from regulator 242, a static memory interface, and a 512 byte programmable read only memory.

The comparator input values are sampled by the microprocessor unit when signaled by a zero crossing detector that the current is at maximum and subtracted from a predetermined value, empirically determined to provide optimum debeaking results. This periodic sampling and subtracting to reduce the predetermined value to zero is, in essence, an integration of the monitored current value and control as a function of the time integral of current. In this manner, the total energy of each burn is maintained at a relatively uniform value despite possible variations in current flow during the burn.

When the predetermined value is reduced to zero or less the microcomputer de-energizes the solid state relay 222 through an output driver. De-energizing the relay 222 simultaneously turns off the ready light 216 and a burn complete light 212 is signaled on by the driver 280.

An operator then removes the bird and after a short interval to perform counting functions, which will be discussed more fully below, the relay is re-energized, the ready light comes on and the process is repeated.

One empirical time/current integral value which has been found to produce desirable debeaking results is 100. Accordingly, for good beak contact with the electrode tips and this steady current flow the resistance burn interval may be 0.1 to 0.2 seconds. When this debeaking rate is compared with previously known rates of 2 or 3 seconds, it will be realized that the subject invention provides a marked improvement in the time required for the debeaking process.

The FIG. 7 embodiment of the subject invention further possesses a communication and record-keeping capability through the multifunction LED display array 202. A variety of performance parameters may be flashed on the display panel from the microcomputers 244 such as the number of debeaks performed since the unit was turned on; the number of debeaks per hour based on the previous two minutes; the number of debeaks in a batch; the energy content of a burn, etc.

The desired display is selected by rolling the rocker arm switch 204 either up or down. A coded value representing the selected display will appear in window 284 and the actual reading will appear in the array of LED windows 285. Moreover, certain parameters may be modified by first selecting the parameter by switch 204 and then modifying the parameter value up or down using rocker switch 206.

In some instances it may be desirable to insure an accurate batch of chicks. In this event a batch count reset button 208 is punched at the beginning of a debeaking process. The desired batch number may be input to the microprocessor and upon debeaking that number a light 214 will be lit to signal completion of the batch.

In one embodiment of the invention information stored in the microprocessor may be fed through a serial link interface 292 to other debeaking units or central communication center for control purposes as desired.

Figure 9:
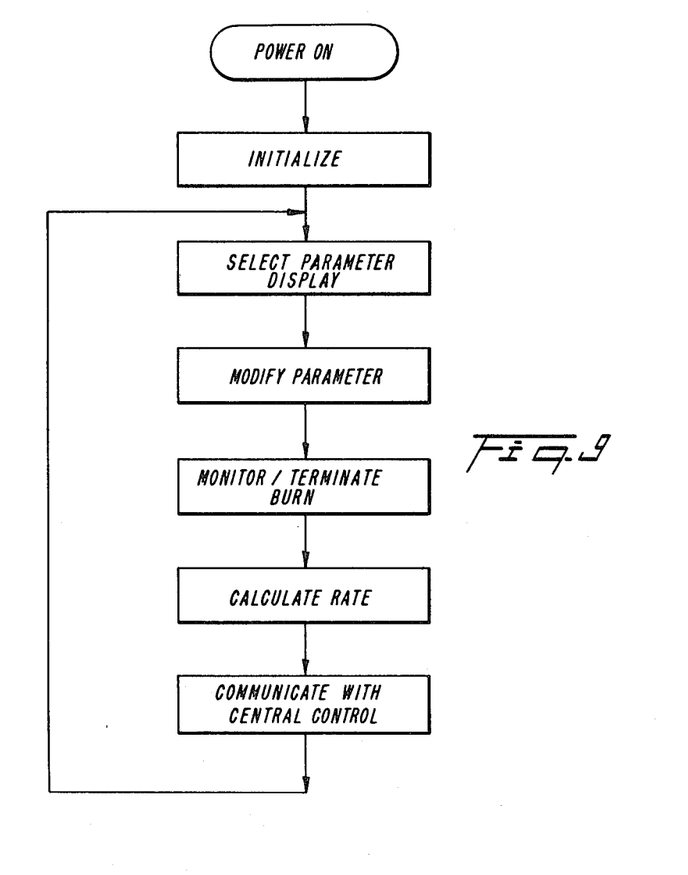
FIG. 9 is a basic flow diagram in accordance with one embodiment of the invention.

Referring now to FIG. 9, there will be seen a basic flow diagram for a debeaking sequence in accordance with an embodiment of the invention.

When the unit is powered on by closing switch 66 the system is initialized. The microcomputer integrated circuits, essentially the microprocessor SMI, and PROM, set up scratch pad memory with default values of burn energy, batch quantity, total (0), rate (0), etc, and performs other preparatory functions prior to entering into debeaker control.

Any one of a plurality of different parameters may be displayed by the debeaker LED array as previously discussed by selection of a parameter code which is rolled up on window 284. Further, a parameter may be modified by rolling the parameter value up or down using the rocker switch 206.

The initiation and progress of burn is monitored by the microcomputer via the analog to digital converter 250 until a prescribed amount of energy is dissipated in the burn or until a maximum time has elapsed, as in an aborted debeaking attempt, whereupon the burn is stopped, the current is turned off momentarily and the relevant counters are updated.

Any calculations of rate, etc. are performed, the information is transmitted to a central control if desired and the control logic is repeated.

In operation an operator axially adjusts the mask means 45 and positions the electrodes, which may be bent or otherwise physically adjusted if need be such that proper location of the electrodes is achieved for the size of the birds to be debeaked. Thus, the terminal tips are spaced apart the approximate thickness of the beak anticipated and at a level adjacent to the upper portion of the beak. The unit is energized by actuation of switch 66 which turns on lamp 68 to signal a ready condition.

A chick's beak is then funneled into mask 50 and into direct physical contact with the electrodes 40, 42.

This completes the circuit and current is passed through the bird's beak which burns a hole through the beak by resistance heating. The burning operation will typically entail less than one second to sufficiently damage the beak and concomitantly cauterize the interior surface. Within a few days the damaged beak portion will continue to deteriorate and the tip of the upper beak will slough off.

In describing a method and apparatus for debeaking domestic fowl in accordance with a preferred embodiment of the invention, those skilled in the art will recognize several advantages which singularly distinguish the invention frrom previously known methods and apparatus.

A particular advantage of the present invention is that the chick's beak is not removed immediately as is the case of the prior art devices but occurs three to five days after the debeaking process. During this interim period the chick is able to eat and drink so as to gain weight and strength. Furthermore, there is no stress to the chick as it is able to normally partake of nourishment.

Another particular advantage of the invention is the provision of electrodes which directly contact and damage the beak tissue.

A further advantage is that the direct contact means provides a relatively low voltage system thereby eliminating the need for a high voltage arc initiation circuit which has been described in one prior art device.

With utilization of the subject invention which damages a mass of tissue through the beak, significant advances in reliability, accuracy, uniformity and permanency of the debeaking process have been achieved. Moreover, these enhanced features have been achieved without requiring an operator to develop a high degree of skill or "feel" for the debeaking process.

Further, the subject method and apparatus effectively isolates an operator from the power system and eliminates a potential shock hazard to the operator. Additonally, the electrode zone is cooled and vaporized beak tissue is withdrawn into an exhaust system and away from an operator's station.

Another significant aspect of the invention is the high rate of debeaking capability as to eliminate major bottleneck in the inoculation/debeaking process.

Still further, the durable mask, preferably quartz, enhances the useful life of the subject unit and the adjustable electrodes minimize down time of the unit for adjustment and attention.

In describing the invention, reference has been made to the preferred embodiment, the best mode as required by the statute. Those skilled in the art, however, and familiar with the disclosure of the subject invention may recognize additions, deletions, modifications, substitutions and/or other changes which will fall within the purview of the subject invention. As an example, it is envisioned that other methods and apparatus for burning a hole through a bird's beak may be practiced in accordance with the invention such as utilization of a coherent beam of light.

What is claimed is:

1. An apparatus for removing an undesired portion of a beak from a fowl comprising:
    mask means for receiving and positioning the beak of the fowl, the mask means having a recess element through which a portion of the beak extends with the beak received by the mask means; and
    means for communicating with the portion of the beak extending through said recess element and for applying energy directly through the interior of said portion of the beak and selectively damaging a portion of said interior extending from one surface to an opposing surface of the beak by heating in said interior, the energy applied through said portion of the beak being of sufficient magnitude to damage said interior portion of the beak by burning without effecting the immediate removal of the undesired portion.

2. The apparatus of claim 1 wherein said means for applying energy constitutes means for burning a hole through said portion of the beak.

* * * * *